United States Patent
Ritter

(10) Patent No.: US 10,449,287 B2
(45) Date of Patent: Oct. 22, 2019

(54) CONCENTRATE CONTAINER FOR AN EXTRACORPOREAL BLOOD TREATMENT MACHINE AND A CONCENTRATE SUPPLY SYSTEM FOR AN EXTRACORPOREAL BLOOD TREATMENT MACHINE

(71) Applicant: B. BRAUN AVITUM AG, Melsungen (DE)

(72) Inventor: Kai-Uwe Ritter, Rednitzhembach (DE)

(73) Assignee: B. Braun Avitum AG (DE)

( * ) Notice: Subject to any disclaimer, the term of this patent is extended or adjusted under 35 U.S.C. 154(b) by 805 days.

(21) Appl. No.: 14/966,072

(22) Filed: Dec. 11, 2015

(65) Prior Publication Data

US 2016/0175512 A1    Jun. 23, 2016

(30) Foreign Application Priority Data

Dec. 18, 2014    (DE) .................. 10 2014 119 106

(51) Int. Cl.
*A61M 1/36*    (2006.01)
*A61M 1/16*    (2006.01)
(Continued)

(52) U.S. Cl.
CPC .......... *A61M 1/367* (2013.01); *A61M 1/1668* (2014.02); *A61M 39/12* (2013.01);
(Continued)

(58) Field of Classification Search
CPC .. A61M 1/3621; A61M 1/367; A61M 1/1668; A61M 39/12; A61M 2039/1027; A61M 2039/1077; A61M 2039/1094; A61M 2206/14; A61M 2206/16; B01F 1/0022; B01F 2005/0091
See application file for complete search history.

(56) References Cited

U.S. PATENT DOCUMENTS

| | | | |
|---|---|---|---|
| 8,123,199 B2 * | 2/2012 | Terentiev | B01F 3/04248 261/93 |
| 8,182,137 B2 | 5/2012 | Terentiev | |

(Continued)

FOREIGN PATENT DOCUMENTS

| | | |
|---|---|---|
| CN | 201076627 Y | 6/2008 |
| CN | 101991885 A | 3/2011 |

(Continued)

OTHER PUBLICATIONS

EP Search Report with translation for EP15198614.8 dated Apr. 22, 2016.
(Continued)

*Primary Examiner* — Philip R Wiest
(74) *Attorney, Agent, or Firm* — RatnerPrestia

(57) ABSTRACT

A concentrate container for an extracorporeal blood treatment machine with a fluid inlet at a first end of the concentrate container and a fluid outlet at a second end of the concentrate container as well as at least one connector to hold a coupling fitting of a fluid conduit, wherein at least one connector is concave in shape and is positioned inside the container. A system for use with this concentrate container, in which the coupling fittings are convex in shape. A connection piece provides for disinfection of the system.

11 Claims, 4 Drawing Sheets

(51) Int. Cl.
*A61M 39/12* (2006.01)
*B01F 1/00* (2006.01)
*B01F 5/00* (2006.01)
*A61M 39/10* (2006.01)

(52) U.S. Cl.
CPC ... *B01F 1/0022* (2013.01); *A61M 2039/1027* (2013.01); *A61M 2039/1077* (2013.01); *A61M 2039/1094* (2013.01); *A61M 2206/14* (2013.01); *A61M 2206/16* (2013.01); *B01F 2005/0091* (2013.01)

(56) References Cited

U.S. PATENT DOCUMENTS

| | | |
|---|---|---|
| 2002/0091371 A1 | 7/2002 | Ritter |
| 2010/0294398 A1 | 11/2010 | Lauer |
| 2011/0041928 A1 | 2/2011 | Völker |
| 2013/0315801 A1* | 11/2013 | Jonsson .............. A61M 1/342 422/554 |
| 2013/0328304 A1 | 12/2013 | Stenzel et al. |
| 2016/0175512 A1 | 6/2016 | Ritter |

FOREIGN PATENT DOCUMENTS

| | | |
|---|---|---|
| CN | 201921180 U | 8/2011 |
| CN | 103463733 A | 12/2013 |
| CN | 205434505 U | 8/2016 |
| DE | 93 02 790.7 | 6/1994 |
| DE | 200 07 278 | 9/2000 |
| DE | 10100549 | 7/2002 |
| WO | WO 00/44418 | 8/2000 |
| WO | 2010121740 | 10/2010 |
| WO | WO 2012/076287 | 6/2012 |

OTHER PUBLICATIONS

German Search Report for German Application No. 10 2014 119 106.4 dated Jul. 27, 2015, including full translation.
Chinese Office Action for Chinese Application No. 201510954070.5, dated Mar. 26, 2019, with translation, 16 pages.

\* cited by examiner

CONCENTRATE CONTAINER FOR AN EXTRACORPOREAL BLOOD TREATMENT MACHINE AND A CONCENTRATE SUPPLY SYSTEM FOR AN EXTRACORPOREAL BLOOD TREATMENT MACHINE

CROSS REFERENCE TO RELATED APPLICATIONS

This application claims priority to German Application No. DE 10 2014 119 106.4 filed Dec. 18, 2014, the contents of such application being incorporated by reference herein.

FIELD OF THE INVENTION

This invention relates to a concentrate container of an extracorporeal blood treatment machine and a concentrate supply system of an extracorporeal blood treatment machine with such a concentrate container.

BACKGROUND OF THE INVENTION

The therapeutic success of hemodialysis is based among other things on the use of various buffering agents so that the altered acid-base balance in patients with renal insufficiency can be corrected. Since the acid-base balance cannot be corrected during dialysis by diffusion or convection, the supply of buffering agents is indispensable. Theoretically, bicarbonate, acetate and lactate are suitable for correcting the imbalance between acids and bases, though due to various disadvantages of lactate and acetate buffering, hemodialysis treatment normally only uses bicarbonate buffering. The buffering agent is the most important component in a dialysate.

In order to diminish the weight of the dialysis machine as well as to reduce the space required for storing the bicarbonate cartridges and prevent any potential contamination of the bicarbonate, the bicarbonate or buffer solution for a medical procedure such as hemodialysis is not produced until immediately before or during treatment.

For this purpose, a container such as a cartridge or capsule containing bicarbonate concentrate powder is connected to a fluid source such as a water source. The water flowing through the cartridge dissolves the bicarbonate concentrate powder stored inside it and flushes it out into the dialysate in doses.

DESCRIPTION OF THE RELATED ART

Such conventional concentrate cartridges as generally known from the state of the art usually comprise a capsule-shaped or cylinder-shaped receptacle with an inlet connector located/configured at its one axial front side or its one axial end to connect the cartridge to a fluid inlet conduit and with an outlet connector at its other axial front side or other end to connect the cartridge to a fluid outlet conduit. These connectors of a conventional concentrate cartridge consist of short tube sections or nozzles protruding (axially) out of the respective cartridge or receptacle, the interior diameter of the tube sections of nozzles being larger than the exterior diameter of the fluid inlet conduit or fluid outlet conduit, so that a fluid conduit can be inserted in a nozzle-shaped connector protruding from the cartridge/receptacle.

However, the conventionally nozzle-shaped connectors of this kind have the disadvantage that they can easily be damaged during transportation of the concentrate cartridges (the protruding connectors can snap/break off, for example), making the cartridge unusable. In addition, more space is required for the cartridges in the transportation container, thereby unnecessarily increasing the logistic costs of the cartridges. The material cost of manufacturing conventional cartridges is also unnecessarily high. After all, the nozzle-shaped connectors have to be elaborately packed in protective material in order to protect them from damage during transportation.

Another disadvantage of conventional concentrate cartridges lies in the fact that the distribution of the fluid flowing into the receptacle via the inlet connector onto the concentrate powder is inadequate. Due to the central axial inflow of the fluid to the concentrate cartridge/receptacle, central axial channel formation along the direction of flow of the fluid can occur in the concentrate powder contained in the cartridge. This results in the concentrate failing to be put to optimum use, since the fluid mainly flows through the channel formed and concentrate deposited on the side walls of the cartridge is not (fully) dissolved. In this way, such channel formation reduces the efficiency of the cartridge and also makes it more difficult to accurately control the concentration of the dissolved substance in the buffer solution. There is also a risk of the cartridges imploding due to channel formation, especially in dialysis machines which generally create negative pressure in the cartridge.

Due to the disadvantageous design of conventional cartridges, the disinfection procedure of the entire system for producing a flow agent (concentrate supply system) carried out after use is very involved. A known system to produce flow agents such as buffer solutions, for example, provides cartridge holders with folding arms on the outside of a dialysis machine. During disinfection of this system or of the dialysis machine, the folding arms are folded in towards the machine side panel and the sockets remain sealed in openings inside the machine side panel, these openings being closed off on the inside of the machine by means of an internal connection piece.

When the folding arms have been folded in in this way, the entire (conduit) system can be flushed for disinfection purposes. Due to the necessity of folding in the folding arms, this procedure is unnecessarily time-consuming, and this configuration also results in undercuts between the folding arms and the cartridge holders which impair cleaning of the system.

Alternatively, in another system for the production of a flow agent known from the state of the art, an external connection piece is inserted between the upper and lower holder of the cartridge. This connection piece is inserted in openings in the holders, which in fact serve to hold the nozzle-shaped inlet-outlet connectors of the cartridge, and is radially sealed from the outside. This insertion of the external connection piece in the relevant openings of the holders makes it more complicated to introduce the connection piece. What is more, the configuration of the radial sealing on the outside of the connection piece unnecessarily increases the size of the connection piece.

SUMMARY OF THE INVENTION

Based on the above-mentioned state of the art, an object of the present invention is firstly to provide a low-cost concentrate container/cartridge in which the fluid (water) flowing through it is optimally distributed onto the concentrate and secondly to simplify the disinfection procedure, carried out after treatment, of a system to produce a flow agent (also referred to as a concentrate supply system).

This object is achieved by means of the concentrate container according to the independent claim and a system for an extracorporeal blood treatment machine to produce a flow agent. Advantageous embodiments and variations of the inventions are the subject of the dependent claims.

The core idea of the invention is therefore to configure the coupling fitting-connector link between a concentrate container (or cartridge) and the fluid inlet and fluid outlet conduits to be connected to it in a way that is based on the socket-plug principle, whereby the socket in the form of the connector is located on the side of the cartridge and the plug in the form of the coupling fitting is located on the side of the conduits. The connector on the cartridge side is configured as a flush-mounted socket which does not protrude out of the wall surface or does so only very slightly.

To put it differently, the respective coupling fitting of a fluid inlet or fluid outlet conduit is configured in the manner of a plug, i.e. as a salient/protruding or convex component. The respective connector of the concentrate container/cartridge which serves to hold a respective coupling fitting of a fluid conduit is configured in the manner of a socket, i.e. a component which is recessed/indented in the concentrate container/receptacle of the cartridge or concave and positioned at least in sections or even entirely inside the concentrate container/receptacle of the cartridge.

In order to connect the concentrate container/cartridge to an extracorporeal blood treatment machine to produce a flow agent such as a bicarbonate buffer solution, for example, the convex/protruding coupling fittings of the fluid inlet and fluid outlet conduits of the extracorporeal blood treatment machine are inserted in the relevant concave connectors/connectors recessed into the relevant concentrate container/receptacle of the cartridge and are mounted inside it at least in sections or even completely.

This has the advantage that the protruding/convex coupling fittings are located on the side of the fluid inlet and fluid outlet conduits on the machine side of the blood treatment machine and do not form part of the concentrate container/cartridge, as is known from the state of the art. As of a result of the fact that the concentrate container/cartridge has no parts (connectors) that protrude from the container wall or which do so only slightly, the space required for transportation and storage of the concentrate containers/cartridges is reduced, as is the risk of damage to the concentrate containers/cartridges. In addition, the material cost of manufacture of the concentrate containers/cartridges is reduced and packaging material is saved. What is more, insertion of the concentrate containers in the system to produce a flow agent such as bicarbonate buffer solution is facilitated since there are no protruding small parts such as the connectors known from the state of the art in the form of nozzle-shaped tube sections protruding from the concentrate containers/receptacles which can be snapped off or damaged in any other way.

In a preferred embodiment, a concentrate container/cartridge according to aspects of the invention comprises a fluid inlet at a first axial end (axial front side of the receptacle of the cartridge), in other words an opening through which fluid (water) can flow into the receptacle. As already suggested above, the fluid inlet is configured as a concave connector protruding into the receptacle of the cartridge, designed to hold a coupling fitting of a fluid conduit. At a second end (axial front side of the receptacle of the cartridge), the concentrate container/cartridge according to aspects of the invention comprises a fluid outlet, i.e. an opening through which the fluid can flow out of the container. The fluid outlet is preferably likewise configured as a concave connector protruding into the receptacle of the cartridge, positioned to hold a coupling fitting of a fluid conduit.

Through the fluid inlet conduit, a fluid such as water flows into the concentrate container/receptacle of the cartridge and dissolves the concentrate inside the concentrate container/receptacle. Via the fluid outlet conduit, the solution consisting of concentrate and water, for example, flows out of the concentrate container/receptacle and can be supplied to a patient, for example as part of an extracorporeal blood treatment.

In order to guarantee that if possible the entire solution flows out of the concentrate container/receptacle and as little solution as possible remains behind in the concentrate container/receptacle, a preferred embodiment is such that the second end (axial front side) of the concentrate container/receptacle, i.e. the axial end of the concentrate container/receptacle of the cartridge, which is connected/connectable to the fluid outlet conduit, is configured as a spherical segment (preferably half-spherical) or cone. Due to this geometrical configuration, the solution collects at the lowest point of the spherical segment or cone. If the fluid outlet of the container is also located at this lowest point, as little solution as possible remains in the concentrate container/receptacle. Due to this configuration of the concentrate container/receptacle, the efficiency of the concentrate container/receptacle is increased.

In order to further improve the efficiency of the concentrate container/receptacle based on optimum utilization of the concentrate, another preferred embodiment of the concentrate container/receptacle additionally comprises a fluid ducting device (flow guidance element) which is positioned downstream in fluid flow direction from at least one connector for holding a coupling fitting of a fluid conduit preferably for fluid inlet into the container. This fluid ducting device serves to direct and regulate the fluid flow so as to counteract channel formation in the concentrate powder. For example, the fluid ducting device separates the stream of fluid flowing into the concentrate container/receptacle into a number of partial streams which are distributed onto the concentrate and/or slows down the fluid flow so that more concentrate is dissolved. When channel formation is prevented in the concentrate container/receptacle in this way, there is less risk of the concentrate container/receptacle imploding, in particular when using it with a blood treatment machine which produces negative pressure in the concentrate container/receptacle, since no uncontrolled hollow spaces such as a central channel are created in the concentrate.

In a preferred embodiment, the fluid ducting device and the connector, which is downstream from the fluid ducting device in fluid flow direction, form an integrated component. This simplifies manufacture of the concentrate container/receptacle and also increases the durability and resilience of the connection between the fluid ducting device and the connector. The component consisting of the fluid ducting device and connector can for example be produced as a single injection-mould part (preferably made of plastic) or as a formed sheet metal part.

In its least complicated embodiment, the fluid ducting device is an impact disc (sprinkler head disc) against which fluid flowing into the container impacts, whereby the fluid is preferably distributed evenly onto the concentrate in the container. Such an impact disc can be configured to be smooth on its surface facing the fluid stream, although it can also comprise structures such as grooves or fins to direct the stream of fluid.

Furthermore, the fluid ducting device can also be pivoted, preferably via a turbine-like impeller wheel. Due to the turning of the fluid ducting device, such as the impact disc, the fluid stream is preferably further subdivided into several partial streams and also deflected in a radial direction so that the fluid also moistens concentrate on the side walls of the concentrate container. In this way, an optimum and even use of the concentrate is enabled and channel formation in the concentrate is counteracted. Instead of a pivot mounting of the fluid ducting device, the radial deflection of the fluid streams can alternatively be effected by the arrangement of the structures such as grooves or fins on the impact disc. The structures can be rounded/curved like turbine blades in a radial direction, for example.

If the fluid stream is only to be slowed down but not radially deflected, however, the fluid ducting device can be configured in another preferred embodiment as a sieve. It is possible to adjust the flow speed of the fluid by varying the mesh size of the sieve.

On the machine side, a (conduit) system for an extracorporeal blood treatment machine for producing a buffer solution which is to be used in conjunction with the above-described concentrate container/cartridge comprises at least one coupling fitting to form a fluid connection between the concentrate container/cartridge and a fluid inlet conduit, and it comprises at least one coupling fitting to form a fluid connection between the concentrate container/cartridge and a fluid outlet conduit. Here, at least one of the coupling fittings but preferably both coupling fittings are convex in configuration (preferably plug/stopper-shaped) and also designed to interlock in the respective concave connector of the concentrate container/cartridge positioned inside the concentrate container/cartridge or to be inserted based on the plug/socket principle.

Since in this system the convex i.e. protruding coupling fittings, in other words the plugs, are provided on the machine side as part of the blood treatment machine, this system does not require the concentrate container/cartridge to be fitted with protruding and easily damaged connection pieces as in the case of the state of the art. Instead, the connectors of the concentrate containers/cartridges according to aspects of the invention are located inside the receptacle of the respective cartridges, are therefore concave in configuration and thus correspond to the plug/socket analogy of the (flush-mounted) socket. Since, unlike the concentrate containers/cartridges, the blood treatment machine is not a disposable item, the convex coupling fittings of the fluid conduits of the blood treatment machine can be configured to be more robust (there is less pressure to reduce material costs), so there is no risk of these coupling fittings snapping off when the concentrate container is inserted.

What is more, in the system according to aspects of the invention, whereby the coupling fittings of the fluid conduits of the blood treatment machine and the connectors of the concentrate containers/cartridges are designed according to the plug/socket principle, insertion of the concentrate container in the blood treatment machine is greatly simplified. This is a considerable benefit in the hectic everyday routine of a hospital.

What is more, disinfection or cleaning and/or rinsing of a (conduit) system is greatly simplified where this system comprises coupling fittings of the fluid conduits of the blood treatment machine and connectors of the concentrate containers/cartridges which are designed according to the plug/socket principle.

After blood treatment using a concentrate container/cartridge, for example, with bicarbonate concentrate, the concentrate container/cartridge is preferably removed from the blood treatment machine and the blood treatment machine is cleaned. Here, an (external) connection piece can be provided to create a connection between the coupling fittings of the fluid inlet conduit and fluid outlet conduit, the connection piece preferably being shaped as a hollow cylinder, of which the internal diameter at least in the area of its two axial end sections is equal to the external diameter of a coupling fitting of a fluid conduit of the system and therefore simulates the connectors of the cartridge that has been removed. This connection piece is mounted on the coupling fittings of the blood treatment machine instead of the concentrate container/cartridge during the disinfection or rinsing process. In this way a fluid connection is formed between the fluid inlet conduit and the fluid outlet conduit (closed circuit) and the blood treatment machine can be rinsed through.

Due to the simplified configuration of the connection/coupling of the convex coupling fittings of the conduits of the blood treatment machine and the concave connectors (protruding into the receptacle of the cartridge) based on the plug/socket principle, the connection piece can also be very easily mounted on the coupling fittings of the blood treatment machine. Here the connection piece structurally replaces the concentrate container/cartridge and the openings of the hollow cylinder of the connection piece constitute "sockets" (connectors) in which the "plugs" (coupling fittings) of the conduits are inserted in each case.

Due to the configuration of the connection/coupling between the coupling fittings of the conduits of the blood treatment machine and the (external) connection piece, the cleaning process of the blood treatment machine is greatly simplified, since for example there are no folding arms to be folded in prior to cleaning and the connection piece does not have to be precisely inserted into recesses in the cartridge holding arms. This makes the cleaning process faster and more user-friendly.

The procedure for disinfecting a system according to aspects of the invention for producing a buffer solution, for example, simplified as compared to the state of the art, in which the coupling fittings of the fluid conduits of the blood treatment machine and the connectors of the concentrate container/cartridge are designed according to the plug/socket principle therefore consists of
- a first stage in which an above-mentioned connection piece is mounted at its axial ends simulating connectors on at least one coupling fitting of the conduit system and
- a second stage in which a process of rinsing the system is carried out.

Here the connection piece can only be mounted on a coupling fitting of the conduit system if the section of the system upstream from the concentrate container is to be rinsed with a different solution, for example, than the part of the system downstream from the concentrate container. For example, only the coupling fitting of the fluid inlet conduit is inserted in the connection piece if the section of the (conduit) system upstream from the concentrate container in the direction of fluid flow is to be rinsed with a different solution than the part of the system downstream from the concentrate container/cartridge. In a further stage, the external connection piece can be connected to the coupling fitting of the fluid outlet conduit and the part of the system downstream from the concentrate container/cartridge can be rinsed separately.

BRIEF DESCRIPTION OF THE DRAWINGS

The invention is best understood from the following detailed description when read in connection with the accompanying drawings. Included in the drawings are the following figures.

In the description of the figures, the same reference numerals in the figures refer to the same or similar components.

DETAILED DESCRIPTION OF THE FIGURES

Figure 1:
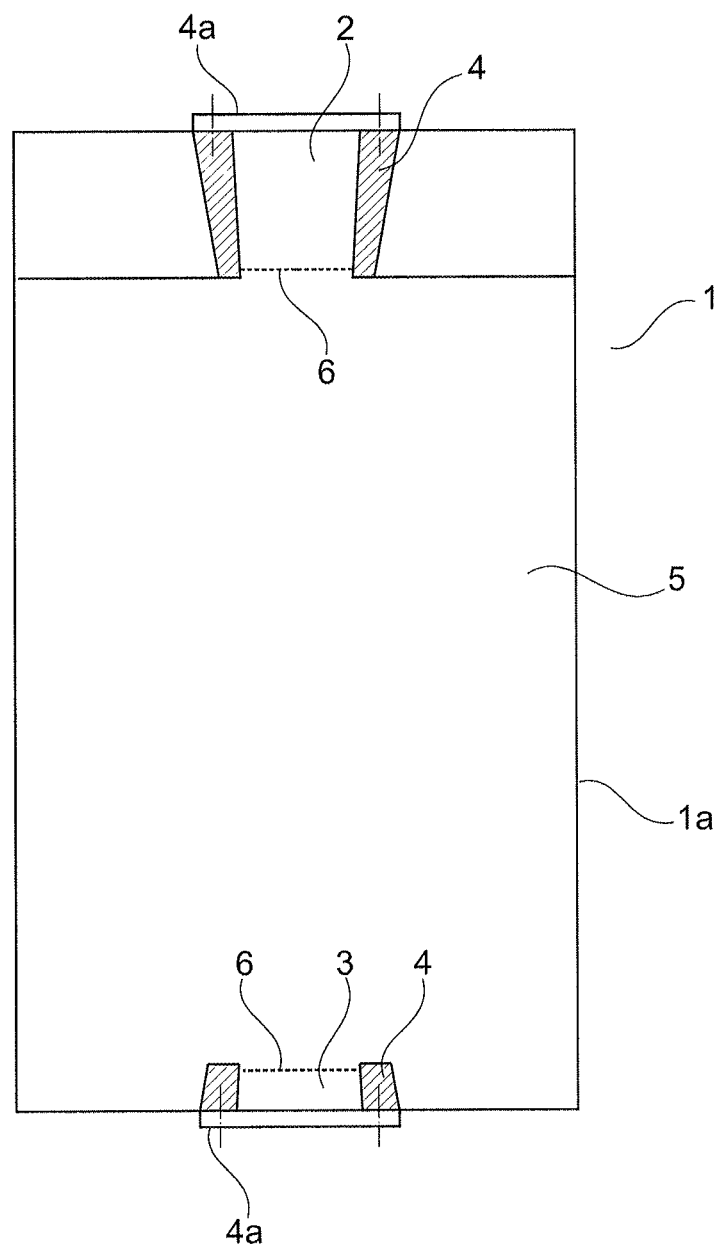
FIG. 1 shows the schematic diagram of a concentrate container/cartridge according to aspects of the invention according to a preferred embodiment of the invention.

FIG. 1 shows a longitudinal section of a concentrate container/cartridge 1 according to aspects of the invention for or of an extracorporeal blood treatment machine (not shown), with a fluid inlet 2 at a first end (first axial front side) of the concentrate container/cylindrical cartridge 1 and a fluid outlet 3 at a second end (second axial front side) of the concentrate container/cartridge 1. The concentrate container/cartridge 1 also has a receptacle 1a essentially shaped as a hollow cylinder for storage of concentrate, on which the fluid inlet 2 and fluid outlet 3 are axially spaced apart. Both the fluid inlet 2 and the fluid outlet 3 are configured in the shape of a sleeve-like connector 4 to hold a coupling fitting 8, 9 of an inlet and outlet fluid conduit (not shown), for example of a blood treatment machine. The connectors 4 are concave in shape and positioned at least partially and preferably entirely inside the receptacle 1a in such a way that the outer periphery of the concentrate container/receptacle 1a is not enlarged by the protrusion of a connector 4, or is only slightly enlarged. The inside of the concentrate container/receptacle 1a is filled with a concentrate 5, preferably in the form of a powder. It is particularly preferable for the concentrate 5 to be bicarbonate powder.

In order to ensure the sterility of the concentrate 5 prior to use of the concentrate container/cartridge 1, both the fluid inlet 2 (i.e. the opening through which the fluid flows into the concentrate container/receptacle 1a when using the concentrate container/cartridge 1) and the fluid outlet 3 (i.e. the opening through which the fluid flows out of the concentrate container/receptacle 1a when using the concentrate container/cartridge 1) are sealed with a membrane 6.

When the concentrate container/cartridge 1 is used to produce a bicarbonate buffer solution, for example, as part of a blood treatment on an extracorporeal blood treatment machine (dialysis machine), the stopper-like coupling fitting 8 of a fluid supply conduit, which supplies fluid to a concentrate container/cartridge 1, is inserted in a sleeve-like connector 4 on the fluid inlet 2 of the concentrate container 1, whereby the membrane 6 sealing the receptacle 1a is also penetrated. In addition, a coupling fitting 9 of a fluid discharge conduit, which drains fluid out of the concentrate container/cartridge 1 and also penetrates the membrane 6, is inserted in the connector 4 on the fluid outlet 3 of the cartridge 1.

If in a particular case such a coupling fitting 8, 9 is inserted in one of the two connectors 4 of the concentrate container/cartridge 1, the seal of the membrane 6 is unavoidably broken on insertion and fluid can flow over the concentrate 5 inside the concentrate container/receptacle 1a and dissolve this concentrate 5. In order to prevent unwanted penetration of the membranes 6, the concentrate container/cartridge 1 can comprise a separate, manually removable cap 4a on its fluid inlet 2 and/or its fluid outlet 3 by means of which the fluid inlet 2 and/or the fluid outlet 3 is protected from parts which might unintentionally pierce the membrane 6.

Figure 1A:
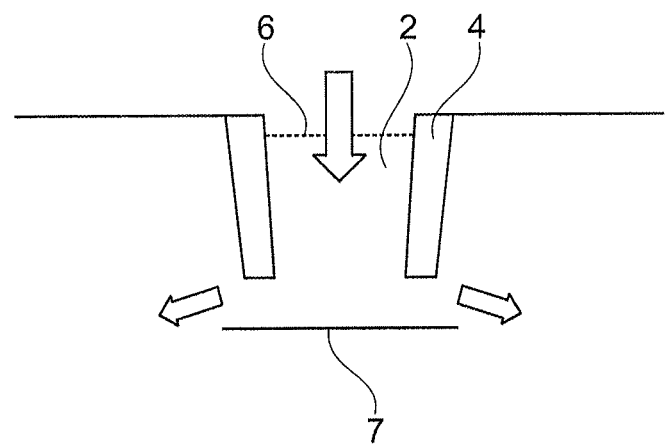
FIG. 1a shows the schematic diagram of a fluid ducting device in the form of an impact disc.
Figure 2:
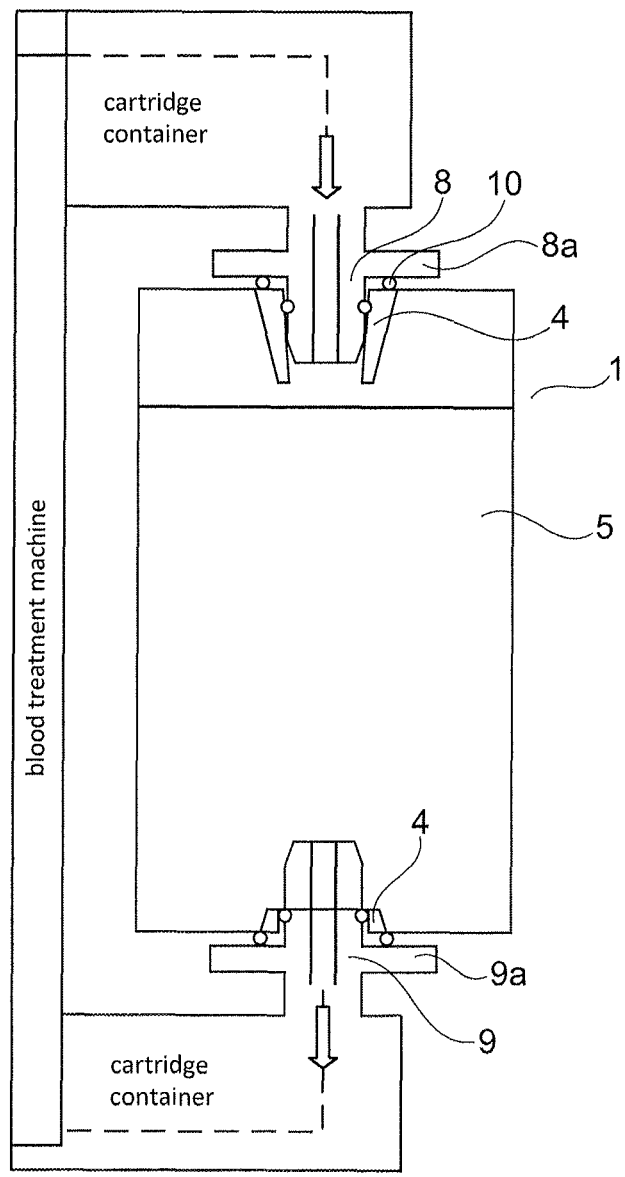
FIG. 2 shows a (conduit) system according to aspects of the invention for an extracorporeal blood treatment machine to produce a buffer solution, for example, with a concentrate container/cartridge according to aspects of the invention

FIG. 1a shows a detailed view of a fluid ducting device in the form of an impact disc 7 which is downstream from a connector 4, preferably on the side of the fluid inlet in the direction of flow of the fluid (thick arrow in FIG. 2). The concentrate container/cartridge 1 from FIG. 1a is shown in a state in which it has not yet been connected to fluid conduits, which is why the membrane 6 at the inlet and outlet is still intact and the fluid inlet 2 and/or fluid outlet 3 of the concentrate container/cartridge 1 is sealed. However, when the coupling fitting 8 of a fluid supply conduit is inserted in the connector 4 of the fluid inlet 2 of the concentrate container/cartridge 1, the relevant membrane 6 is penetrated by the coupling fitting 8 and fluid flows in the fluid flow direction (thick arrow) into the receptacle is of the cartridge 1. Directly after the fluid inlet 2, however, the fluid hits the impact disc 7, whereby the flow of fluid is slowed down and/or subdivided into several partial streams which are each deflected radially outwards (shown by the two smaller, thin arrows) from the original direction of flow of the fluid (thick arrow). This impact disc 7 prevents uncontrolled (axial) channel formation in the concentrate 5 due to a constant central, axial flow of fluid through the concentrate 5 in the direction of flow of the fluid (thick arrow). The efficiency of the concentrate container/cartridge 1 is also enhanced because, for example, concentrate 5 on the side walls of the hollow cylinder of the concentrate container/receptacle 1, i.e. concentrate 5 which is radially outside the original direction of flow of the fluid (thick arrow), is also moistened by the fluid.

Figure 1B:
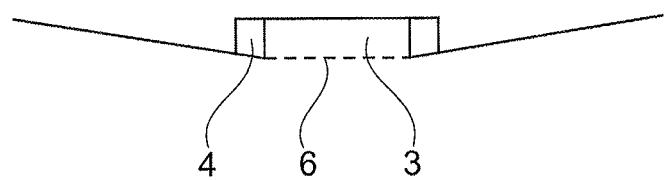
FIG. 1b shows a cone-shaped configuration of an end of a concentrate container/cartridge according to aspects of the invention comprising the fluid outlet.

FIG. 1b shows a detailed view of a concentrate container/cartridge 1 in which the axial end (front side) of the concentrate container 1 with the fluid outlet 3 is configured in the shape of a truncated cone or curved outwards. This geometric configuration of the concentrate container 1 has the effect of ensuring that as much of the fluid as possible flows out of the concentrate container 1. For this purpose, the fluid outlet 3 is placed at the lowest point of the truncated cone-shaped/curved base of the concentrate container/cartridge 1. This detailed view also shows a concentrate container/cartridge 1 before use so that the membranes 6 are still intact.

FIG. 2 shows a system according to aspects of the invention for an extracorporeal blood treatment machine (dialysis machine) for producing a buffer solution, for example, with a concentrate container/cartridge 1 according to aspects of the invention. In addition to the concentrate container/cartridge 1 according to aspects of the invention, this system comprises a coupling fitting 8 to form a fluid connection between the concentrate container/cartridge 1 and the fluid inlet conduit or fluid supply conduit, and at least the coupling fitting 9 to form a fluid connection between the concentrate container/cartridge 1 and the fluid outlet conduit or fluid discharge conduit. In this system, the two coupling fittings 8 and 9 are convex in configuration, i.e. designed in a shaft-like manner as components which preferably protrude axially from the conduit ends in the manner of a plug, bung or stopper. For this reason, the two coupling fittings 8 and 9 are designed to interlock with or to be inserted into the respective concave connector 4 of the concentrate container/cartridge 1, the connector 4 being located inside the concentrate container/cartridge 1 and protruding into the receptacle 1a of the cartridge 1 like a sleeve or socket.

As shown in FIG. 2, the two coupling fittings 8 and 9 are inserted in the two connectors 4, the membranes 6 (not shown) have been broken through and fluid can flow in the direction of flow of the fluid (thick arrow) through the concentrate container/receptacle 1a. Sealing devices such as O-rings 10, for example, are used to seal the plug connection between a respective coupling fitting 8, 9 and a connector 4. Here the sealing is preferably effected by two O-rings 10 per connection/coupling between the coupling fitting 8, 9 and the connector 4. An O-ring 10 is located inside the concentrate container/cartridge 1 in the opening of the fluid inlet 2 or the fluid outlet 3, radially inward from the connector 4 between the connector 4 and the respective coupling fitting 8, 9. In other words, this O-ring acts as a radial seal, sealing a ring gap between the coupling fitting 8, 9 and the sleeve-shaped connector 4. The second O-ring 10 forms a seal between the outer surface (axial front side) of the concentrate container/receptacle 1a and a radial flange section 8a, 9a of the respective coupling fitting 8, 9, thereby acting as an axial seal which seals the axial gap between the front side of the receptacle 1a and the flange/collar 8a, 9a of the coupling fitting 8, 9.

Figure 3:
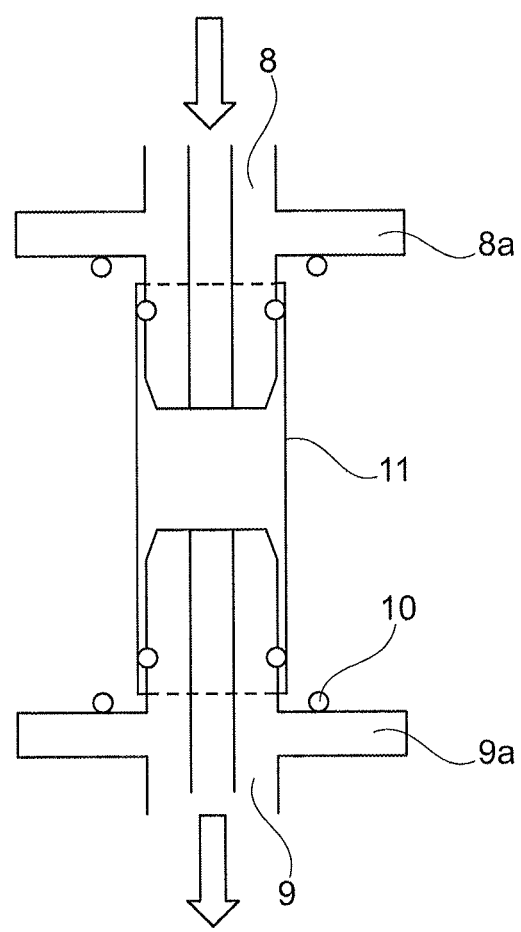
FIG. 3 shows an external connection piece for insertion in or which is insertable in a (conduit) system according to aspects of the invention for an extracorporeal blood treatment machine to produce a buffer solution, for example, instead of a cartridge according to aspects of the invention, in particular for the purpose of cleaning/disinfection.

FIG. 3 shows a connector 11 which is inserted during cleaning/disinfection of the extracorporeal blood treatment machine in a (conduit) system according the invention for an extracorporeal blood treatment machine for producing a buffer solution, for example. The connector 11 is configured for this purpose as a hollow cylinder and is placed on the coupling fittings 8, 9 of the (conduit) system according to aspects of the invention instead of the concentrate container/cartridge 1. For this purpose, a connector is simulated at both axially spaced ends of the connection piece 11 which is designed to hold the coupling fittings of the (conduit) system on the machine side.

When the connection piece 11 is placed with its axial ends on the coupling fittings 8, 9 so as to close them off, it is possible to duct a cleaning fluid in the direction of flow of the fluid (thick arrow) through the (conduit) system according to aspects of the invention for an extracorporeal blood treatment machine. Sealing of the connection between the connection piece 11 and the coupling fittings 8, 9 is by means of an O-ring 10 which is placed as a ring seal between the radial inner wall of the hollow cylinder of the connection piece 11 and the radial outer wall of the coupling fitting 8, 9 inserted in the connection piece 11 so as to seal the ring gap formed at this point.

The invention claimed is:

1. A cartridge-shaped concentrate container for an extracorporeal blood treatment machine having at least one fluid conduit, comprising:

a receptacle having a first axial end and a second axial end;
a fluid inlet on the first axial end of the receptacle; and
a fluid outlet on the second axial end of the receptacle;
wherein at least one of the fluid inlet or the fluid outlet comprises a concave connector located inside the cartridge-shaped concentrate container, wherein the concave connector is configured to couple with a corresponding fluid conduit of the extracorporeal blood treatment machine, the concave connector protruding at least partially into the receptacle,
the cartridge-shaped concentrate container further comprising a fluid ducting device positioned downstream of fluid flow from the connector,
wherein the fluid ducting device comprises structures for the selective deflection of the flowing fluid, and
wherein the connector and the fluid ducting device form a single, integral component.

2. The cartridge-shaped concentrate container of claim 1, wherein the concave connector protrudes completely into the receptacle with partial external axial overhang.

3. The cartridge-shaped concentrate container of claim 1, wherein the concave connector protrudes partially into the receptacle without any external axial overhang.

4. The cartridge-shaped concentrate container of claim 1, wherein the second axial end of the receptacle is configured in the shape of a spherical shell segment or a truncated cone.

5. The cartridge-shaped concentrate container of claim 1, wherein the fluid ducting device is an impact disc against which fluid flowing into the receptacle impacts, whereby the fluid is spread in a radially even manner onto a concentrate deposited in the concentrate container.

6. The cartridge-shaped concentrate container of claim 1, wherein the fluid ducting device is pivoted by means of a turbine-like impeller wheel.

7. The cartridge-shaped concentrate container of claim 1, wherein the fluid ducting device is configured as a sieve.

8. A conduit system for an extracorporeal blood treatment machine for producing a flow agent, comprising:
the cartridge-shaped concentrate container of claim 1; and
at least one inlet coupling fitting to form a fluid connection between the cartridge-shaped concentrate container and a fluid inlet conduit of the conduit system; and
at least one outlet coupling fitting to form a fluid connection between the cartridge-shaped concentrate container and a fluid outlet conduit of the conduit system;
wherein at least one of the coupling fittings is convex in shape and is configured to engage with a corresponding concave connector positioned inside the receptacle of the cartridge-shaped concentrate container.

9. The conduit system of claim 8, wherein the fluid ducting device comprises structures for the selective deflection of the flowing fluid.

10. The conduit system of claim 9, wherein the fluid ducting device is an impact disc against which fluid flowing into the receptacle impacts, whereby the fluid is spread in a radially even manner onto the concentrate deposited in the concentrate container.

11. The cartridge-shaped concentrate container of claim 1, wherein the fluid inlet is sealed with a membrane, and the fluid ducting device is separated from the membrane at a position downstream of the membrane.

* * * * *